(12) United States Patent
Schmidt et al.

(10) Patent No.: US 8,772,041 B2
(45) Date of Patent: Jul. 8, 2014

(54) MEMBRANE PRECURSORS AND MEMBRANES FORMED THEREFROM

(75) Inventors: Jacob J. Schmidt, Sherman Oaks, CA (US); Tae-Joon Jeon, Incheon (KR); Jason L. Poulos, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 729 days.

(21) Appl. No.: 12/993,713

(22) PCT Filed: May 22, 2009

(86) PCT No.: PCT/US2009/044979
§ 371 (c)(1),
(2), (4) Date: Feb. 1, 2011

(87) PCT Pub. No.: WO2009/143425
PCT Pub. Date: Nov. 26, 2009

(65) Prior Publication Data
US 2011/0118489 A1 May 19, 2011

Related U.S. Application Data

(60) Provisional application No. 61/055,274, filed on May 22, 2008.

(51) Int. Cl.
*G01N 33/92* (2006.01)
(52) U.S. Cl.
USPC ............................. 436/71; 977/756; 977/757
(58) Field of Classification Search
None
See application file for complete search history.

(56) References Cited

U.S. PATENT DOCUMENTS

| | | | |
|---|---|---|---|
| 4,661,442 A * | 4/1987 | Lukens | 435/4 |
| 6,436,905 B1 | 8/2002 | Tonge | 514/23 |
| 6,682,893 B2 | 1/2004 | Taylor | 435/6 |
| 6,699,952 B2 | 3/2004 | Chaikof | 526/277 |
| 6,846,352 B2 | 1/2005 | Yatake | 106/31.58 |
| 6,846,795 B2 | 1/2005 | Lant | 510/446 |
| 6,849,426 B2 | 2/2005 | Chen | 435/69.1 |
| 6,852,816 B2 | 2/2005 | Lewis | 526/277 |
| 6,863,833 B1 * | 3/2005 | Bloom et al. | 216/2 |
| 6,913,697 B2 * | 7/2005 | Lopez et al. | 210/644 |
| 7,479,483 B2 | 1/2009 | Ponzoni | 514/12 |
| 7,638,092 B2 | 12/2009 | Ide | 436/5 |
| 7,939,270 B2 * | 5/2011 | Holden et al. | 435/7.1 |
| 8,038,885 B2 | 10/2011 | Schmidt | 210/645 |
| 8,242,077 B2 | 8/2012 | Lakey | 514/17.4 |
| 8,513,165 B2 * | 8/2013 | Takeuchi et al. | 506/33 |
| 2002/0081617 A1 | 6/2002 | Buranda | 435/7.5 |
| 2003/0175824 A1 | 9/2003 | Pishko | 435/7.2 |
| 2005/0154374 A1 | 7/2005 | Hunter | 424/401 |
| 2006/0160066 A1 | 7/2006 | Bhatia | 435/29 |
| 2012/0025414 A1 | 2/2012 | Schmidt | 210/645 |

FOREIGN PATENT DOCUMENTS

| | | | |
|---|---|---|---|
| EP | 09751653.8 | 12/2010 | |
| EP | 11732112.5 | 7/2012 | |
| EP | 12006905.9 | 10/2012 | |
| WO | PCT/US2000/025627 | 9/2000 | |
| WO | PCT/US2002/011312 | 4/2002 | |
| WO | PCT/US2006/034199 | 8/2006 | |
| WO | WO 2007/047498 | * 4/2007 | ............... B05D 3/00 |
| WO | PCT/US2009/044979 | 5/2009 | |
| WO | PCT/US2011/020284 | 1/2011 | |

OTHER PUBLICATIONS

Hromada L.P. et al., "Single molecule measurements within individual membrane-bound ion channels using a polymer-based bilayer lipid membrane chip", Lab on a Chip (2008) 8:602-608.*
Jeon, Tae-Joon et al., "Hydrogel-encapsulated lipid membranes", Journal of the American Chemical Society (2006) 128:42-43.*
Jeon Tae-Joon, "Storable and transporable lipid bilayer membrane precursor", Abstract of Papers, 235$^{th}$ ACS National Meeting, (Apr. 2008) Coll171.*
Jeon Tae-Joon et al., "Long-term storable and shippable lipid bilayer membrane platform", Lab on a Chip (2008) 8:1742-1744.*
Malmstadt, N. et al., "Automated formation of lipid-bilayer membranes in a microfluidic device", Nano Letters (2006) 6(9):1961-1965.*
Poulos, J.L., "Automatable lipid bilayer formation for ion channel studies", Proceedings of SPIE (2008) 7035:703509.*
U.S. Appl. No. 13/520,339, filed Jan. 5, 2011, Jason L. Poulos.
U.S. Appl. No. 13/646,305, filed Oct. 5, 2012, Jacob J. Schmidt.
Akeson et al., "Microsecond Time-Scale Discrimination Among Polycytidylic Acid, Polyadenylic Acid, and Polyuridylic Acid as Homopolymers or as Segments Within Single RNA Molecules," *Biophys J* 1999, 77:3227-3233.
Albertero et al., "The α,α-(1→1) Linkage of Trehalose is Key to Anhydrobiotic Preservation," *J Am Chem Soc* 2007, 129(34):10567-10574.
Alexandridis, "Amphiphilic copolymers and their applications," *Curr Opin Colloid Interface Sci* 1996, 1(4):490-501.
Andersson et al., "TRPM8 Activation by Menthol, Icilin, and Cold is Differentially Modulated by Intracellular pH," *J Neurosci* 2004, 24:5364-5369.
Anrather et al., "Supported Membrane Nanodevices," *J Nanosci Nanotech* 2004, 4(1/2):1-22.

(Continued)

*Primary Examiner* — Bao Thuy L Nguyen
*Assistant Examiner* — Gary E Hollinden
(74) *Attorney, Agent, or Firm* — Ballard Spahr LLP (57) ABSTRACT

Disclosed are biomimetic membrane precursors and membranes formed therefrom. Also disclosed are methods of making biomimetic membrane precursors and membranes formed therefrom. Methods of using, including methods of storing and handling biomimetic membrane precursors and membranes formed therefrom, are also disclosed.

19 Claims, 4 Drawing Sheets

(56) References Cited

OTHER PUBLICATIONS

Baaken et al., "Nanopore-Based Single-Molecule Mass Spectrometry on a Lipid Membrane Microarray," *ACS Nano* 2011, 5:8080-8088.
Baaken et al., "Planar microelectrode-cavity array for high-resolution and parallel electrical recording of membrane ionic currents," *Lab Chip* 2008, 8:938-944.
Bainbridge et al., "Voltage gating is a fundamental feature of porin and toxin beta-barrel membrane channels," *FEBS Lett* 1998, 431(3):305-308.
Bautista et al., "The menthol receptor TRPM8 is the principal detector of environmental cold," *Nature* 2007, 448:204-208.
Bayley et al., "Droplet interface bilayers," *Mol Biosyst* 2008, 4:1191-1208.
Bayley et al., "Stochastic sensors inspired by biology," *Nature* 2001, 413(6852):226-230.
Beddow et al., "Reconstitution of nicotinic acetylcholine receptors into gel-protected lipid membranes," *Anal Chem* 2004, 76(8):2261-2265.
Behrendt et al., "Characterization of the mouse cold-menthol receptor TRPM8 and vanilloid receptor type-1 VR1 using a fluorometric imaging plate reader (FLIPR) assay," *Br J Pharmacol* 2004, 141:737-745.
Blake et al., "Monitoring chemical reactions by using ion-channel-forming peptides," *Chembiochem* 2006, 7:433-435.
Blaustein et al., "Anthrax Toxin—Channel-Forming Activity of Protective Antigen in Planar Phospholipid-Bilayers," *Proc Natl Acad Sci USA* 1989, 86:2209-2213.
Braha et al., "Designed protein pores as components for biosensors," *Chemistry and Biology* 1997, 4:497-505.
Braha et al., "Simultaneous stochastic sensing of divalent metal ions," *Nature Biotechnology* 2000, 18:1005-1007.
Brauchi et al., "Clues to understanding cold sensation: Thermodynamics and electrophysiological analysis of the cold receptor TRPM8," *Proc Natl Acad Sci USA* 2004, 101:15494-15499.
Brohawn et al., "Crystal structure of the human K2P TRAAK, a lipid- and mechano-sensitive K+ ion channel," *Science* 2012, 335(6067):436-441.
Canal et al., "Correlation between mesh size and equilibrium degree of swelling of polymeric networks," *J Biomed Mater Res* 1989, 23(10):1183-1193.
Capone et al., "Designing Nanosensors Based on Charged Derivatives of Gramicidin A," *J Am Chem Soc* 2007, 129:9737-9745.
Chachin et al., "Epinastine, a nonsedating histamine H1 receptor antagonist, has a negligible effect on HERG channel," *Eur J Pharmacol* 1999, 374(3):457-460.
Cheley et al., "Stochastic sensing of nanomolar inositol 1,4,5-trisphosphate with an engineered pore," *Chem Biol* 2002, 9:829-838.
Chen et al., "Position of aromatic residues in the S6 domain, not inactivation, dictates cisapride sensitivity of HERG and eag potassium channels," *Proc Natl Acad Sci* 2002, 99(19):12461-12466.
Cheng et al., "A high-throughput HERG potassium channel function assay: An old assay with a new look," *Drug Dev Indust Pharm* 2002, 28(2):177-191.
Chiu et al., "Validation of a [3H]astemizole binding assay in HEK293 cells expressing HERG K+ channels," *J Pharmacol Sci* 2004, 95(3):311-319.
Chuang et al., "The super-cooling agent icilin reveals a mechanism of coincidence detection by a temperature-sensitive TRP channel," *Neuron* 2004, 43:859-869.
Cohen, "Fusion of phospholipid vesicles with planar phospholipid bilayer membranes. II. Incorporation of a vesicular membrane marker into the planar membrane," *J Gen Physiol* 1980, 75:251-270.
Colburn et al., "Attenuated cold sensitivity in TRPM8 null mice," *Neuron* 2007, 54:379-386.
Comley, "Patchers verses screener: divergent opinion on high throughput electro-physiology," *Drug Discovery World* 2003, 47-57.
Costello et al., "Improved gel-protected bilayers," *Biosensors Bioelectronics* 1999, 14(3):265-271.

Diaz et al., "The [3H]dofetilide binding assay is a predictive screening tool for hERG blockade and proarrhythmia: Comparison of intact cell and membrane preparations and effects of altering [K+]," *J Pharmacol Toxicol Methods* 2004, 50(3):187-199.
Dragoni et al., "The Cold and Menthol Receptor TRPM8 Contains a Functionally Important Double Cysteine Motif," *J Biol Chem* 2006, 281:37353-37360.
Dunlop et al., "High-throughput electrophysiology: an emerging paradigm for ion-channel screening and physiology," *Nature Reviews Drug Discovery* 2008, 7:358-368.
Eccles, "Methanol and related cooling compounds," *J Pharm Pharmacol* 1994, 46:618-630.
El-Arabi et al., "Ion channel drug potency assay with an artificial bilayer chip," *Lab Chip* 2012, 12(13):2409-2413.
Falconer et al., "High-Throughput Screening for Ion Channel Modulators," *J Biomolec Screen* 2002, 7(5):460-465.
Favero et al., "Membrane supported lipid bilayer membranes array: preparation, stability and ion-channel insertion," *Analytica Chimica Acta* 2002, 460(1):23-34.
Fernández et al., "Voltage- and cold-dependent gating of single TRPM8 ion channels," *J Gen Physiol* 2011, 137:173-195.
Funakoshi et al., "Lipid bilayer formation by contacting monolayers in a microfluidic device for membrane protein analysis," *Anal Chem* 2006, 78:8169-8174.
Golowasch et al., "Allosteric effects of Mg2+ on the gating of Ca2+-activated K+ channels from mammalian skeletal muscle," *J Exp Biol* 1986, 124(1):5-13.
Gu et al., "Stochastic sensing of organic analytes by a pore-forming protein containing a molecular adapter," *Nature* 1999, 398:686-690.
Guan et al., "Stochastic sensing of TNT with a genetically engineered pore," *Chembiochem* 2005, 6:1875-1881.
Han et al., "Nanopore Arrays for Stable and Functional Free-Standing Lipid Bilayers," *Adv Mater* 2007, 19:4466-4470.
Hancox et al., "The hERG potassium channel and hERG screening for drug-induced torsades de pointes," *Pharmacol Therapeut* 2008, 119(2):118-132.
Hanke & Schlue, "Planar Lipid Bilayers: Methods and Applications," *Academic Press*, London; New York 1993.
Hartgerink et al., "Self-Assembly and Mineralization of Peptide-Amphiphile Nanofibers," *Science* 2001, 294(5547):1684-1688.
Hartgerink et al., "Supramolecular Chemistry and Self-assembly Special Feature: Peptide-amphiphile nanofibers: A versatile scaffold for the preparation of self-assembling materials," *Proc Natl Acad Sci* 2002, 99(8):5133-5138.
Heron et al., "Direct detection of membrane channels from gels using water-in-oil droplet bilayers," *J Am Chem Soc* 2007, 129(51):16042-16047.
Hertzberg & Pope, "High-throughput screening: new technology for the 21st century," *Curr Opin Chem Biol* 2000, 4:445-451.
Hirano et al., "Lipid Bilayers at Gel/Gel Interface for Ion Channel Recordings," *J Surf Sci Nanotech* 2008, 6:130-133.
Holden et al., "Functional bionetworks from nanoliter water droplets," *J Am Chem Soc* 2007, 129:8650-8655.
Hu et al., "2-Aminoethoxydiphenyl borate is a common activator of TRPV1, TRPV2, and TRPV3," *J Biol Chem* 2004, 279:35741-35748.
Hwang et al., "Asymmetric droplet interface bilayers," J Am Chem Soc 2008, 130:5878-5879.
Ide et al., "Lipid Bilayers at the Gel Interface for Single Ion Channel Recordings," *Anal Chem* 2008, 80(20):7792-7795.
Ide et al., "Simultaneous Optical and Electrical Recording of a Single Ion-Channel," *Japanese J Physiol* 2002, 52:429-434.
Ide et al., "An Artificial Lipid Bilayer Formed on an Agarose-Coated Glass for Simultaneous Electrical and Optical Measurement of Single Ion Channels," *Biochem Biophys Res Commun* 1999, 265:595-599.
Ionescu-Zanetti et al., "Mammalian electrophysiology on a microfluidic platform," *Proc Natl Acad Sci USA* 2005, 102:9112-9117.
Jacobson et al., "Microchip structures for submillisecond electrophoresism" *Analyt Chem* 1998, 70:3476.
Jeon et al., "Black lipid membranes stabilized through substrate conjugation to a hydrogel," *Biointerphases* 2008, 3:96-100.

(56) References Cited

OTHER PUBLICATIONS

Joanicot et al., "Droplet control for microfluidics," *Science* 2005, 309(5726):887-888.
Kang et al., "A Storable Encapsulated Bilayer Chip Containing a Single Protein Nanopore," *J Am Chem Soc* 2007, 129(15):4701-4705.
Kasianowicz et al., "Characterization of individual polynucleotide molecules using a membrane channel," *Proc Natl Acad Sci USA* 1996, 93:13770-13773.
Kazakov et al., "UV-induced gelation on nanometer scale using liposome reactor," *Macromolecules* 2002, 35(5):1911-1920.
Keating et al., "Molecular and Cellular Mechanisms of Cardiac Arrhythmias," *Cell* 2001, 104:569-580.
Kedei et al., "Analysis of the native quaternary structure of vanilloid receptor 1," *J Biol Chem* 2001, 276:28613-28619.
Kiehn et al., "Cellular and Molecular Cardiology: Molecular Physiology and Pharmacology of HERG: Single-Channel Currents and Block by Dofetilide," *Circulation* 1996, 94(10):2572-2579.
Kloxin et al., "Photodegradable Hydrogels for Dynamic Tuning of Physical and Chemical Properties," *Science* 2009, 324(5923):59-63.
Knoll et al., "Functional tethered lipid bilayers," *Rev Mol Biotech* 2000, 74(3):137-158.
Krishna et al., "Tethered Bilayer Membranes Containing Ionic Reservoirs: Selectivity and Conductance," *Langmuir* 2003, 19:2294-2305.
Krylov et al., "Water Permeability of Asymmetric Planar Lipid Bilayers—Leaflets of Different Composition Offer Independent and Additive Resistances to Permeation," *JPG* 2001, 118(4):333-340.
Kuhner et al., "Lipid mono- and bilayer supported on polymer films: composite polymer-lipid films on solid substrates," *Biophys J* 1994, 67(1):217-226.
Lashinger et al., "AMTB, a TRPM8 channel blocker: evidence in rats for activity in overactive bladder and painful bladder syndrome," *Am J Physiol Renal Physiol* 2008, 295:803-810.
Le Pioufle et al., "Lipid bilayer microarray for parallel recording of transmembrane ion currents," *Anal Chem* 2008, 80:328-332.
Lee et al., "Solvent compatibility of poly(dimethylsiloxane)-based microfluidic devices," *Anal Chem* 2003, 75(23):6544-6554.
Lee et al., "Photoreversible viscosity changes and gelation in mixtures of hydrophobically modified polyelectrolytes and photosensitive surfactants," *Macromolecules* 2004, 37:5397-5405.
Leptihn et al., "In Vitro Reconstitution of Eukaryotic Ion Channels using Droplet Interface Bilayers," *J Am Chem Soc* 2011, 133:9370-9375.
Liu & Qin, "Functional control of cold- and menthol-sensitive TRPM8 ion channels by phosphatidylinositol 4,5-bisphosphate," *J Neurosci* 2005, 25:1674-1681.
Long et al., "Atomic structure of a voltage-dependent K+ channel in a lipid membrane-like environment," *Nature* 2007, 450:376-382.
Lu et al., "Biophysical aspects of agar-gel supported bilayer lipid membranes: a new method for forming and studying planar bilayer lipid membranes," *Bioelectrochem Bioenergetics* 1996, 39:285-289.
Lustig et al., "Solute Diffusion in Swollen Membranes .9. Scaling Laws for Solute Diffusion in Gels," *J Appl Polymer Sci* 1988, 36(4):735-747.
Malmstadt et al., "Automated formation of lipid-bilayer membranes in a microfluidic device," *Nano Letters* 2006, 6:1961-1965.
Malmstadt et al., "New approaches to lipid bilayer fabrication: microfluidic solvent extraction and hydrogel encapsulation," *Adv Sci Technol* 2006, 53:22-31.
Malmstadt et al., "Long-Lived Planar Lipid Bilayer Membranes Anchored to an In Situ Polymerized Hydrogel," *Adv Mater* 2008, 20(1):84-89.
Martens et al., "Tailoring the degradation of hydrogels formed from multivinyl poly(ethylene glycol) and poly(vinyl alcohol)macromers for cartilage tissue engineering," *Biomacromolecules* 2003, 4:283-292.
Matthews et al., "Design and fabrication of a micromachined planar patch-clamp substrate with integrated microfluidics for single-cell measurements," *J MEMS* 2006, 15:214-222.
Mayer et al., "Microfabricated teflon membranes for low-noise recordings of ion channels in planar lipid bilayers," *Biophys J* 2003, 85:2684-2695.
Mayer et al., "Using ion channel-forming peptides to quantify protein-ligand interactions," *J Am Chem Soc* 2008, 130:1453-1465.
Maynard et al., "Thermoresponsive biohybrid materials synthesized by ATRP," *J Mater Chem* 2007, 17:4015-4017.
McDonald et al., "Poly(dimethylsiloxane) as a material for fabricating microfluidic devices," *Acct Chem Res* 2002, 35(7):491-499.
McKemy et al., "Identification of a cold receptor reveals a general role for TRP channels in thermosensation," *Nature* 2002, 416:52-58.
Meller et al., "Rapid nanopore discrimination between single polynucleotide molecules," *Proc Natl Acad Sci* 2000, 97:1079-1084.
Miller, "Ion Channel Reconstitution." Plenum Press, New York 1986.
Molokanova et al., "Bright future of optical assays for ion channel drug discovery," *Drug Discovery Today* 2008, 13:14-22.
Montal et al., "Formation of Bimolecular Membranes from Lipid Monolayers and a Study of Their Electrical Properties," *Proc Natl Acad Sci* 1972, 69(12):3561-3566.
Moscho et al., "Rapid preparation of giant unilamellar vesicles," *Proc Natl Acad Sci* 1996, 93:11443-11447.
Mueller et al., "Reconstitution of cell membrane structure in vitro and its transformation into an excitable system," *Nature* 1962, 194(4832):979-980.
Mueller et al., "Reconstitution of excitable cell membrane structure in vitro," *Circulation* 1962, 26:1167-1171.
Nakane et al., "Nanopore sensors for nucleic acid analysis," *J Phys Condensed Matter* 2003, 15(32):R1365-R1393.
Naumowicz et al., "Impedance analysis of phosphatidylcholine membranes modified with gramicidin D," *Bioelectrochem* 2003, 61:21-27.
Nilius, "TRP channels in disease," *Biochimica Et Biophysica Acta-Molecular Basis of Disease* 2007, 1772:805-812.
Ottova & Tien, "Self-assembled bilayer lipid membranes: from mimicking biomembranes to practical applications," *Bioelectrochem Bioenergetics* 1997, 42:141-152.
Peier et al., "A TRP Channel that Senses Cold Stimuli and Menthol," *Cell* 2002, 108:705-715.
Perez et al., "Reconstitution of Expressed K-Ca Channels from Xenopus-Oocytes to Lipid Bilayers," *Biophys J* 1994, 66:1022-1027.
Portonovo & Schmidt, "Masking apertures enabling automation and solution exchange in sessile droplet lipid bilayers," *Biomed Microdevices* 2011, 14:187-191.
Poulos et al., "Ion channel and toxin measurement using a high throughput lipid membrane platform," *Biosens Bioelectron* 2009, 24:1806-1810.
Poulos et al., "Automatable lipid bilayer formation for ion channel studies," SPIE Proceedings 2008, 7035 (6 pages).
Poulos et al., "Automatable production of shippable bilayer chips by pin tool deposition for an ion channel measurement platform" *Biotechnol J* 2010, 5:511-514.
Poulos et al., "Electrowetting on dielectric-based microfluidics for integrated lipid bilayer formation and measurements," *Appl Phys Lett* 2009, 95 (3 pages).
Poulos et al., "Automatable lipid bilayer formation and ion channel measurement using sessile droplets," *J Phys: Condens Matter* 2010, 22:454105.
Purnell et al., "Nucleotide Identification and Orientation Discrimination of DNA Homopolymers Immobilized in a Protein Nanopore," *NanoLetters* 2008, 8(9):3029-3034.
Rehak et al., "Examination of bilayer lipid membranes for 'pin-hole' character," The Analyst 2004, 129:1014-1025.
Rohács et al., "PI(4,5)P2 regulates the activation and desensitization of TRPM8 channels through the TRP domain," *Nat Neurosci* 2005, 8:626-634.
Rosenbaum et al., "Subunit modification and association in VR1 ion channels," *BMC Neurosci* 2002, 3:4-13.
Sakmann & Neher, "Patch clamp techniques for studying ionic channels in excitable membranes," *Ann Rev Physiol* 1984, 46:455-472.
Sakmann & Neher (eds.), "Single-channel recording," Plenum Press, New York 1995.
Sandison et al., "Air-exposure technique for the formation of artificial lipid bilayers in microsystems," *Langmuir* 2007, 23:8277-8284.

(56) References Cited

OTHER PUBLICATIONS

Sandison et al., "Micromachined glass apertures for artificial lipid bilayer formation in a microfluidic system," *J Micromech Microeng* 2007, 17:S189-S196.
Sandison et al., "Rapid fabrication of polymer microfluidic systems for the production of artificial lipid bilayers," *J Micromech Microeng* 2005, 15:S139-S144.
Schein et al., "Reconstitution in planar lipid bilayers of a voltage-dependent anion-selective channel obtained from paramecium mitochondria," *J Membrane Biol* 1976, 30(1):99-120.
Schindler & Rosenbusch, "Matrix Protein from *Escherichia coli* Outer Membranes Forms Voltage-Controlled Channels in Lipid Bilayers," *Proc Natl Acad Sci* 1978, 75(8):3751-3755.
Schindler & Quast, "Functional acetylcholine receptor from Torpedo marmorata in planar membranes," *Proc Natl Acad Sci* 1980, 77(5):3052-3056.
Schindler, "Formation of Planar Bilayers from Artificial or Native Membrane-Vesicles," *FEBS Lett* 1980, 122:77-79.
Schmalhofer et al., "A Pharmacologically Validated, High-Capacity, Functional Thallium Flux Assay for the Human Ether-à-go-go Related Gene Potassium Channel," *Assay Drug Dev Technol* 2010, 8(6):714-726.
Shim et al., "Stochastic Sensing on a Modular Chip Containing a Single Ion Channel," *Anal Chem* 2007, 79(6):2207-2213.
Sia et al "Microfluidic devices fabricated in poly(dimethylsiloxane) for biological studies," *Electrophoresis* 2003, 24(21):3563-3576.
Sinner et al., "Functional tethered membranes," *Curr Opinion Chem Biol* 2001, 5(6):705-711.
Song et al., "Millisecond kinetics on a microfluidic chip using nanoliters of reagents," *J Am Chem Soc* 2003, 125(47):14613-14619.
Song et al., "Structure of staphylococcal alpha-hemolysin, a heptameric transmembrane pore," *Science* 1996, 274(5294):1859-1866.
Suarezisla et al., "Single-Channel Recordings from Purified Acetylcholine-Receptors Reconstituted in Bilayers Formed at the Tip of Patch Pipets," *Biochemistry* 1983, 22:2319-2323.
Suzuki et al., "Electrophysiological recordings of single ion channels in planar lipid bilayers using a polymethyl methacrylate microfluidic chip," *Biosens Bioelectron* 2007, 22:1111-1115.
Suzuki et al., "Highly reproducible method of planar lipid bilayer reconstitution in polymethyl methacrylate microfluidic chip," *Langmuir* 2006, 22:1937-1942.
Suzuki et al., "Planar lipid bilayer reconstitution with a microfluidic system," *Lab Chip* 2004, 4:502-505.
Syeda et al., "Screening Blockers Against a Potassium Channel with a Droplet Interface Bilayer Array," *J Am Chem Soc* 2008, 130:15543-15548.
Takagi et al., "A new method for the formation of bilayer membranes in aqueous solutions," *Ann Rep Biol Fac Sci Osaka* 1965, 13:107-110.
Tao & MacKinnon, "Functional analysis of Kv1.2 and paddle chimera Kv channels in planar lipid bilayers," *J Mol Biol* 2008, 382:24-33.
Terrettaz et al., "Highly Electrically Insulating Tethered Lipid Bilayers for Probing the Function of Ion Channel Proteins," *Langmuir* 2003, 19:5567-5569.
Thapliyal et al., "Automated lipid bilayer and ion channel measurement platform," *Biosens Bioelectron* 2011, 26:2651-2654.
Thorsen et al., "Dynamic pattern formation in a vesicle-generating microfluidic device," *Phys Rev Lett* 2001, 86(18):4163-4166.
Thorsen et al., "Microfluidic large-scale integration," *Science* 2002, 298:580-584.
Titus et al., "A new homogeneous high-throughput screening assay for profiling compound activity on the human ether-a-go-go-related gene channel," *Analyt Biochem* 2009, 394(1):30-38.
Trenor et al., "Photoreversible Chain Extension of Poly(ethylene glycol)," *Macromolec Chem Phys* 2004, 205(6):715-723.
Tsavaler et al., "Trp-p8, a novel prostate-specific gene, is up-regulated in prostate cancer and other malignancies and shares high homology with transient receptor potential calcium channel proteins," *Cancer Res* 2001, 61:3760-3769.

Tsofina et al., "Production of Bimolecular Protein-Lipid Membranes in Aqueous Solution," *Nature* 1966, 212:681-683.
Unger et al., "Monolithic microfabricated valves and pumps by multilayer soft lithography," *Science* 2000, 288(5463):113-116.
Vodyanoy et al., "Alamethicin-Induced Current-Voltage Curve Asymmetry in Lipid Bilayers," *Biophys J* 1983, 42:71-82.
Wang et al., "Development of a novel solid-phase extraction element for thermal desorption gas chromatography analysis," *J Chrom A* 2004, 1035(2):277-279.
Weigl et al., "Lab-on-a-chip for drug development," *Adv Drug Delivery* 2003, 55:349-377.
White, "The physical nature of planar bilayer membranes," in *Ion Channel Reconstitution*, Plenum Press, New York 1986, pp. 3-35.
Wonderlin et al., "Optimizing Planar Lipid Bilayer Single-Channel Recordings for High-Resolution with Rapid Voltage Steps," *Biophys J* 1990, 58:289-297.
Wong et al., "Single molecule measurements of channel proteins incorporated into biomimetic polymer membranes," *Nanotechnology* 2006, 17:3710-3717.
Wulff et al., "Voltage-gated potassium channels as therapeutic targets," *Nat Rev Drug Discov* 2009, 8(12):982-1001.
Yuan et al., "Bilayer Thickness Modulates the Conductance of the BK Channel in Model Membranes," *Biophys J* 2004, 86(6):3620-3633.
Zagnoni et al., "Bilayer lipid membranes from falling droplets," *Anal Bioanal Chem* 2009, 393:1601-1605.
Zagnoni et al., "Microfluidic array platform for simultaneous lipid bilayer membrane formation," *Biosens Bioelectron* 2009, 24:1235-1240.
Zakharian et al., "Gating of Transient Receptor Potential Melastatin 8 (TRPM8) Channels Activated by Cold and Chemical Agonists in Planar Lipid Bilayers," *J Neurosci* 2010, 30:12526-12534.
Zakharian et al., "Inorganic polyphosphate modulates TRPM8 channels," *PLoS One* 2009, 4 (12 pages).
Zhang & Barritt, "TRPM8 in prostate cancer cells: a potential diagnostic and prognostic marker with a secretory function?" *Endocr Relat Cancer* 2006, 13:27-38.
Zheng et al., "Screening of protein crystallization conditions on a microfluidic chip using nanoliter-size droplets," *J Am Chem Soc* 2003, 125(37):11170-11171.
Zholos, "Pharmacology of transient receptor potential melastatin channels in the vasculature," *Brit J Pharmacol* 2010, 159:1559-1571.
Zhou et al., "Properties of HERG channels stably expressed in HEK 293 cells studied at physiological temperature," *Biophys J* 1998, 74(1):230-241.
Zou et al., "Single HERG delayed rectifier K+ channels expressed in Xenopus oocytes," *Am J Physiol-Heart Circ Physiol* 1997, 272(3):H1309-H1314.
Preliminary Amendment filed Apr. 11, 2008 for U.S. Appl. No. 12/083,410, filed Oct. 13, 2006 and later granted as US Patent No. 8,038,885 on Oct. 18, 2011 (Inventors—Jacob J. Schmidt et al.) (10 pages).
Requirement for Restriction/Election issued Oct. 4, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (7 pages).
Response to Election/Restriction filed Nov. 10, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (9 pages).
Non-Final Rejection issued Nov. 18, 2010 for U.S. Appl. No. 12/083,410, filed Oct. 13, 2006 and later granted as U.S. Patent No. 8,038,885 on Oct. 18, 2011 (Inventors—Jacob J. Schmidt et al.) (7 pages).
Response to Non-Final Rejection filed May 6, 2011 for U.S. Appl. No. 12/083,410, filed Oct. 13, 2006 and later granted as U.S. Patent No. 8,038,885 on Oct. 18, 2011 (Inventors—Jacob J. Schmidt et al.) (13 pages).
Notice of Allowance issued Jun. 16, 2011 for U.S. Appl. No. 12/083,410, filed Oct. 13, 2006 and later granted as U.S. Patent No. 8,038,885 on Oct. 18, 2011 (Inventors—Jacob J. Schmidt et al.) (13 pages).

(56) References Cited

OTHER PUBLICATIONS

International Search Report issued May 3, 2007 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (2 pages).
Written Opinion issued May 3, 2007 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (5 pages).
International Preliminary Report on Patentability issued Apr. 16, 2008 by the International Searching Authority for Application PCT/US2006/040200 filed Oct. 13, 2006, which published as WO 2007/047498 on Apr. 26, 2007 (Applicant—The Regents of the University of California // Inventors—Jacob J. Schmidt, et al.) (6 pages).
Communication Pursuant to Rules 161(2) and 162 EPC issued Aug. 14, 2012 for European Application No. 11732112.5, which is a national phase of PCT/US2011/020284, filed Jan. 5, 2011 and later published as WO 2011/085047 on Jul. 14, 2011 (Applicant—The Regents of the University of California // Inventors—Jason L. Poulos, et al.) (2 pages).
International Search Report issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (2 pages).
Written Opinion issued Mar. 21, 2011 by the International Searching Authority for Application PCT/US2011/020284 filed Jan. 5, 2011, which published as WO 2011/085047 on Jul. 14, 2011 (Applicant—The Regents of the University of California // Inventors—Jason L. Poulos, et al.) (8 pages).
International Preliminary Report on Patentability issued Jul. 10, 2012 by the International Bureau for Application PCT/US2011/020284 filed Jan. 5, 2011, which published as WO 2011/085047 on Jul. 14, 2011 (Applicant—The Regents of the University of California // Inventors—Jason L. Poulos, et al.) (9 pages).
Voluntary Amendment filed Nov. 7, 2012 for European Application No. 12006905.9 filed on Oct. 5, 2012, which claims priority to U.S. Appl. No. 61/543,771 (Applicant—The Regents of the University of California // Inventors—Jacob J. Schmidt, et al.) (16 pages).
Voluntary Amendment filed Dec. 22, 2010 for European Application No. 09751653.8, which is a national phase of PCT/US2009/044979, filed May 22, 2009 and later published as WO 2009/143425 on Nov. 26, 2009 (Applicant—The Regents of the University of California // Inventors—Jacob J. Schmidt, et al.) (3 pages).
Communication Pursuant to Rules 161(2) and 162 EPC issued Jan. 14, 2011 for European Application No. 09751653.8, which is a national phase of PCT/US2009/044979, filed May 22, 2009 and later published as WO 2009/143425 on Nov. 26, 2009 (Applicant—The Regents of the University of California // Inventors—Jacob J. Schmidt, et al.) (2 pages).
International Search Report issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (3 pages).
Written Opinion issued Oct. 26, 2009 by the International Searching Authority for Application PCT/US2009/044979 filed May 22, 2009, which published as WO 2009/143425 on Nov. 26, 2009 (Applicant—The Regents of the University of California // Inventors—Jacob J. Schmidt, et al.) (4 pages).
International Preliminary Report on Patentability issued Nov. 23, 2010 by the International Bureau for Application PCT/US2009/044979 filed May 22, 2009, which published as WO 2009/143425 on Nov. 26, 2009 (Applicant—The Regents of the University of California // Inventors—Jacob J. Schmidt, et al.) (5 pages).

\* cited by examiner

MEMBRANE PRECURSORS AND MEMBRANES FORMED THEREFROM

CROSS REFERENCE TO RELATED APPLICATIONS

This application claims the benefit of priority to U.S. Provisional Application 61/055,274, filed May 22, 2008, which is incorporated by reference herein in its entirety.

FIELD

Disclosed herein are compositions, methods, and devices related to membranes, their formation, and their use.

BACKGROUND

Artificially reconstituted freestanding planar lipid bilayers play an important role in ion channel electrophysiological studies and are used in pharmaceutical and sensor applications. The technological utility of lipid membranes can be limited, however, by their characteristic short lifetime and fragility. These shortcomings have necessitated membrane formation be at the time and point of use.

Recently, research has focused on the creation of lipid bilayer membranes of two primary varieties: freestanding (communicating with fluid on each side) and solid-supported (communicating with a fluid one side and a surface on the other). Freestanding membranes can be made using traditional "painting" methods, in which the membrane precursor is dissolved in an organic solution and spread over an orifice. These membranes are difficult to form, have short lifetimes, and are fragile. In solid supported membranes it can be problematic to measure trans-membrane ionic transport electrically because of the inaccessibility of one side of the membrane. Furthermore, since the solid support stabilizes the membrane extremely well, defects in the membrane can occur without any effect on the rest of the membrane, which can severely complicate transport measurements.

Although recent work with gel encapsulation has improved membrane robustness and lifetime significantly (Jeon et al., *J. Am. Chem. Soc.* 128:42-43, 2006; Kang et al., *J. Am. Chem. Soc.* 129:4701-4705, 2007; Shim and Gu, *Anal. Chem.* 79:2207-2213, 2007; Malmstadt et al., *Adv. Mat.* 20:84-89, 2008) a degree of membrane longevity, robustness, and portability compatible with commercial shipping has not yet been demonstrated. Furthermore, the process of membrane formation (Mueller et al., *Nature*, 194:979-980, 1962; Montal and Mueller, *Proc. Nat. Acad. Sci. U.S.A.* 69:3561-3566, 1972) still requires significant operator involvement for chamber assembly and the membrane formation process, limiting manufacturability. Microfluidic devices capable of creating and measuring lipid bilayers require manipulation of multiple aqueous/air/organic fluidic phases or their manual deposition to facilitate lipid bilayer membrane formation.

Therefore, there remains a need for methods, compositions, and devices that overcome these deficiencies and that effectively provide for membranes and/or membrane precursors with improved robustness, stability, and longevity. The methods, compositions, and devices disclosed herein address these and other needs.

SUMMARY

In accordance with the purposes of the disclosed materials, compositions, articles, devices, and methods, as embodied and broadly described herein, the disclosed subject matter, in one aspect, relates to devices, compounds and compositions and methods for preparing and using such devices, compounds and compositions. Also disclosed are membrane precursors and membranes formed therefrom. Also disclosed are methods of making freestanding membranes and membrane precursors for freestanding membranes. Methods of using, including methods of storing and handling membrane precursors and membranes formed therefrom, are also disclosed. Still further, devices that can be used to form membranes are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several embodiments and together with the description serve to explain the principles of the invention.

DETAILED DESCRIPTION

Before the present articles, devices, compounds, compositions, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a membrane," "the polymer," or "an agent" includes mixtures of two or more such membranes, polymers, or agents, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Reference will now be made in detail to specific aspects of the disclosed materials, compounds, compositions, articles, and methods, examples of which are illustrated in the accompanying Examples.

Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components or residues A, B, and C are disclosed as well as a class of components or residues D, E, and F, and an example of a combination compound A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Membrane Precursors

In one aspect, described herein is a membrane precursor and also membranes, e.g., lipid bilayers, made therefrom. The membrane precursors disclosed herein comprise a lipid and a reversible lipid immobilizer.

Lipids

A "lipid" as used herein is a molecule composed of hydrophilic and hydrophobic groups (i.e., an amphiphile). In one example, a membrane precursor can comprise mixtures of two or more lipids. Suitable lipids can be generally classified as ionic (anionic/cationic/dipolar) and nonionic. More specifically, polymeric surfactants, silicon surfactants, fluorinated surfactants, oligomeric surfactants, dimeric surfactants, natural lipids, and the like, are suitable lipids for the devices and methods disclosed herein.

In one aspect, the membrane precursors disclosed herein can comprise an anionic lipid. Any anionic lipid can be used. Suitable anionic lipids are commonly used in detergents, shampoos, soaps, etc., and can be obtained commercially or prepared by methods known in the art. They include, but are not limited to, alkylbenzene sulfonates (detergent), fatty acid based surfactants, lauryl sulfate (e.g., a foaming agent), di-alkyl sulfosuccinate (e.g., a wetting agent), lignosulfonates (e.g., a dispersant), and the like, including mixtures thereof. In other examples, linear alkylbenzene sulphonic acid, sodium lauryl ether sulphate, alpha olefin sulphonates, phosphate esters, sodium sulphosuccinates, hydrotropes, and the like, including mixtures thereof, can be used.

In another aspect, the membrane precursors disclosed herein can comprise a cationic lipid. Any cationic lipid can be used. Suitable cationic lipids included, but are not limited to, quaternary ammonium compounds (e.g., tetraalkyl ammonium salts, pyridinium salts, imidazolinium salts, and the like). Such cationic lipids can be obtained commercially or can be prepared by methods known in the art.

In still another aspect, the membrane precursors disclosed herein can comprise a nonionic lipid. Any nonionic lipid can be used. Suitable nonionic lipids do not ionize in aqueous solution, because their hydrophilic group is of a non-dissociable type, such as alcohol, phenol, ether, ester, or amide. They can be classified as ethers (e.g., polyhydric alcohols such as glycerin, solbitole, sucrose, etc.), fatty acid esters (e.g., glycerin fatty acid ester, sobitan fatty acid ester, sucrose fatty acid ester, etc.), esters (e.g., compounds made by applying, for example, ethylene oxide to a material having hydroxyl radicals such as high alcohol, alkyl-phenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanol-amide type or the alkylpolyglyceride type). Other suitable examples of nonionic lipids can include, but are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, etc.

In yet another aspect, the membrane precursors disclosed herein can comprise dipolar lipids. Any dipolar lipid can be used. Suitable dipolar lipids (called amphoteric or zwitterionic) exhibit both anionic and cationic dissociation. Suitable examples of dipolar lipids include, but are not limited to, products like betaines or sulfobetaines and natural substances such as amino acids and phospholipids. In one aspect, the betaines disclosed in U.S. Pat. Nos. 6,852,816; 6,846,795; 6,846,352; and 6,849,426, which are incorporated by reference in their entireties, can be used herein.

Other examples of suitable lipids include natural surfactants, which can have their source from plant or animal organs. In another example, a bolaform lipids can be used. A bolaform lipid is a lipid that has two hydrophilic head groups at opposite ends of a hydrophobic tail.

Mixtures of these lipids can also be used in the compositions and methods disclosed herein.

In one specific example, the disclosed membrane precursors comprises diphytanoylphosphatidylcholine and/or 1,2-diphytanoyl-sn-glycero-3-phosphatidylcholine.

Lipid Immobilizer

A "lipid immobilizer" is a composition that can immobilize a lipid as disclosed herein. Preferably, the lipid immobilizer can immobilize a lipid in a reversible manner. That is, the immobilizer can, under one set of conditions, prevent the lipid from forming a membrane and then, under another set of conditions, allow the lipid to associate into a membrane (e.g., lipid bilayer). The conditions for immobilization are used when the membrane precursor is in storage or being shipped. The conditions where the immobilization of the lipid is reversed are used when one desires the lipid to form a membrane (e.g., at the time of use).

A lipid immobilizer can be one or more of a solvent, polymer, or hydrogel that at one set of conditions forms a solid or hydrogel that immobilizes lipid and at another set of conditions forms a liquid that allows the lipid to assemble into a membrane. The change from solid to liquid forms can be produced by a change in light, temperature, pressure, pH, and the like.

Solvents

Disclosed herein are lipid bilayer formation strategies that can utilize, for example, temperature control over the process of lipid bilayer self assembly. In one example, a high freezing point lipid-containing solvent can be used. In this example, membrane precursor comprising a lipid solution can be frozen prior to the completion of the spontaneous process of bilayer self-assembly, a process which can optionally be resumed by thawing and allowing membrane formation to resume. Thus, in certain examples, the lipid immobilizer can comprise one or more solvents. Suitable solvent(s) are those that dissolve the lipid, allow the lipid to form a membrane, and reversibly solidify in a way that leaves the surrounding aqueous solution unchanged (e.g., the melting point is not so low that water also freezes). Preferably solvent with high melting points (e.g., above about 4, 10, 15, 20, 25, 35, 40, 45, 50, 60, or 70° C. can be used. Examples of suitable solvents include, but are not limited to, nonane, decane, dodecane, tetradecane, hexadecane, squalene, cyclohexane, polyvinyl alcohol, lauric acid, acetic acid, formic acid, benzene, naphthalene, nitrobenzene, phenol, ethylene bromide, and the like, including mixtures thereof. In one specific example, the immobilizer comprises hexadecane and decane in an 8:2 ratio.

Hydrogels

In other examples, the reversible lipid immobilizer comprises a hydrogel. A hydrogel is a three-dimensional polymer network composed of homopolymers or copolymers that are capable of absorbing large amounts of water. Thus, a characteristic of hydrogels is that they swell in water or aqueous fluids without dissolving.

Suitable hydrogels can be obtained commercially or prepared by methods known in the art. Examples of suitable hydrogels that can be used in the disclosed methods include, but are not limited to, polymers based on diol- or glycol-containing linkages, for example, polyethylene glycol (PEG), also known as polyethylene oxide (PEO), and polypropylene oxide (PPO). Other suitable examples include polyesters that are polymerized with PEG to form a hydrogel with multiple segments or blocks of PEG alternating with blocks of polyester. Other examples include polyhydroxyalkanoates, polypropylene fumarate, polyvinylpyrrolidone, poly-N-methylpyrrolidone, hydroxypropylcellulose, carboxypolymethylene, polyhydroxypropyl methacrylate, polyhydroxyethyl methacrylate, polyacrylate, polyacrylamide, poly-N-isopropylacrylamide, poly-N,N-dimethylacrylamide, poly(hydroxy ethylmethacrylate), poly-2-hydroxypropyl methacrylamide, and mixtures thereof. In still other examples, suitable hydrogels include aminodextran, dextran, carboxymethyl dextran, DEAE-dextran, chondroitin sulfate, dermatan, dermatan sulfate, heparan, heparin, heparan sulfate, chitosan, polyethyleneimine, polylysine, alginic acid, sodium alginate, pectin, gelatin, acid-hydrolytically-degraded gelatin, collagen, hyaluronic acid, agarose, carrageenan, starch, polyvinyl alcohol, cellulose, methylcellulose, carboxymethylcellulose, polyacrylic acid, polyethylene glycol, polyethylene glycol diacrylate, polyethylene glycol dimethacrylate, and mixtures thereof.

In some preferred examples, the lipid immobilizer can be a hydrogel that turns into liquid when exposed to light. Examples of these hydrogels are PEG hydrogels with nitrobenzyl ether linker, which irreversibly form liquids upon light exposure (*Science* 324:59-63, 2009), and PEG with coumarin chain ends, which reversibly form liquids upon light exposure (*Macromolecular Chemistry and Physics* 205: 715-723, 2004). Still further examples are liquids that turn into hydrogels when exposed to light. There are numerous examples of such liquids, such as multi-vinyl PEGs with vinyl chain ends, which irreversibly form hydrogels upon exposure to light (*Biomacromolecules* 4:283-292 2003), and polyelectrolytes with cationic azobenzene surfactant, which reversibly form hydrogels upon exposure to light (*Macromolecules* 37:5397-5405, 2004). In yet further examples, the lipid immobilizer can be a liquid that turns into a gel when temperature goes above room temperature (about 25° C.). Examples of such liquids are numerous and include poly-N-isopropyl acrylamide and its copolymers (*Journal of Materials Chemistry* 17:4015-4017, 2007), and pluronics, which are block copolymers of polypropylene oxide and PEG (PPO-PEG-PPO) (*Current Opinion Colloid Interface Science* 1:490-501, 1996). Suitable lipid immobilizers also include gels that turn into liquid with increasing temperature (e.g., above about 4° C.). Many polymers have this property if they are not covalently or ionically crosslinked, for example gelatin. Self-assembling amphiphilic peptides can also be used as lipid immobilizers (*Science* 294:1684-1689, 2001; *PNAS* 99:5133-5138, 2002). All references referred to in this paragraph are incorporated by reference herein for their teachings of hydrogels, gels, and liquids.

Secondary Components

The membrane precursor can optionally comprise one or more secondary components. Examples of such secondary components include, but are not limited to, a ligand (e.g., a potential therapeutic agent, a small molecule, an agonist, an antagonist, an inhibitor, an activator, a suppressor, a stimulator, and the like), a protein (e.g., a receptor, a channel, a signal transducer, an enzyme (e.g., a kinase, a phosphatase, a reductase, an oxidase), and the like), an antibody, a nucleic acid (e.g., a prime, probe, aptamer, ribozyme, and the like hybridizing to a target sequence of a nucleic acid), and the like, including mixtures thereof. Other suitable secondary components can include, but are not limited to, preservatives, antioxidants, stabilizers, and the like, including mixtures thereof.

Devices for Preparing Membranes

In one aspect, disclosed herein is a device for forming a membrane. The devices, as well as the methods, disclosed herein involve a substrate comprising a microfluidic channel, wherein the microfluidic channel comprises a membrane precursor. The membrane precursor, as described above is a combination of a lipid and lipid immobilizer, such as a lipid-solvent mixture, that can form a membrane. Specifically, the lipids used to form the membrane precursor, and thus membrane, are dissolved in a suitable lipid immobilizer, as disclosed elsewhere herein, and the resulting mixture is placed into a microfluidic channel, e.g., across the microfluidic channel orifice, and immobilized (e.g., by freezing or forming a hydrogel). This allows the membrane precursor to be stored indefinitely. Upon reversing the immobilization, the membrane precursor forms a membrane in the microfluidic channel. Preferable, the channel provides access for electrical measurements on both sides of the formed membrane.

Figure 1A:
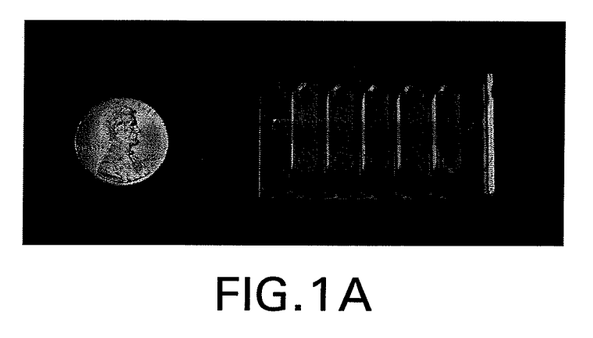
FIG. 1 is a group of photographs of (a) an acrylic chip used for membrane formation. The penny shown is about the same size and cost of the apparatus and solution. The lipid solution, deposited on the 500 μm diameter aperture in the partition, was cooled to 4° C. and frozen (b). Heating to 20° C. thawed the solution (c) which proceeded to spontaneously thin to a bilayer membrane (d).
Figure 1B:
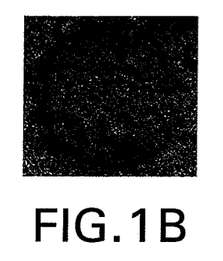
Figure 1C:
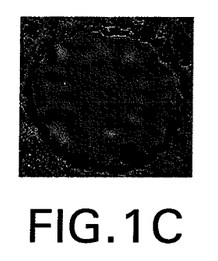
Figure 1D:
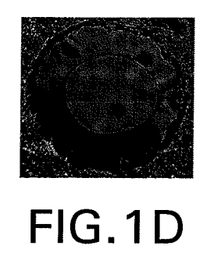
Figure 4:
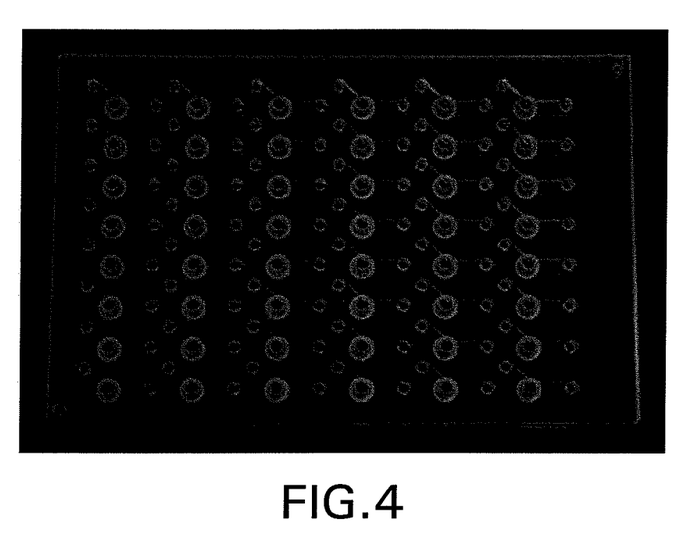
FIG. 4 is a photograph of a multichannel device for membrane formation.

As noted, the disclosed devices involve a substrate with one or more microfluidic channels (see FIG. 1a and FIG. 4). The microfluidic channels can be separate or they can be interconnected to form a network of channels. It is contemplated that the disclosed devices are not limited by the particular order, identity, or arrangement, of the microfluidic channel.

The components of the disclosed device should be compatible with the particular lipids, solvents, analytes, and reagents with which the device is to be used and come in contact with. For example, the device can be used to form and analyze lipid bilayers; hence, the device should not react with, degrade, or have any deleterious impact on the particular compounds that are to be analyzed. Also, the device should be stable towards and resist degradation from typical solvents used in biological chemical applications and preparations.

Substrate

As noted above, the disclosed devices comprise a substrate. The substrate typically functions as a support or matrix for the microfluidic channels. The substrate of the device can be made of material that is readily commercially available and/or can be prepared by methods known to one of ordinary skill in the art. The substrate can be made from any material that does not affect, interfere with, or in anyway diminish the devices particular end use purposes. Thus, substrate materials that could react with, change, alter, or degrade a desired lipid or analyte for which the device is being used should be avoided.

Suitable materials for the substrate can include, but are not limited to, silicon (single crystal or polycrystalline), coatings on silicon (e.g., silicon nitride), silicone, glass, quartz, platinum, stainless steel, copper, aluminum, nickel, gold, titanium, ceramics, diamond, and/or plastics. Examples of suitable plastics include polyolefins (e.g., polyethylene, polypropylene, polystyrene, poly(meth)acrylate, polymethyl (meth)acrylate, polydivinylbenzene, fluorinated polydivinylbenzene, poly-N-vinylpyrrolidone, or mixtures thereof), polyesters (e.g., polyethylene terephthalate), cellulose acetate, polyamides (e.g., nylon), polyimide, and/or polycarbonate. In a specific example, the substrate can comprise polydimethylsiloxane. In another example, the substrate can comprise TEFLON™ or an acrylic. The particular substrate to be used in a particular device can be determined by one of skill in the art based on the particular end use purposes of the device.

Microfluidic Channels

The disclosed devices comprise one or more microfluidic channels on or in the substrate. Microfluidic channels are fluidic channels with at least one dimension (width, height, and length) on the micrometer scale (i.e., greater than about 1 µm but less than about 1 mm. Incorporating microfluidic channels on or in a substrate can be performed by standard photolithographic, etching, deposition, embossing, laminar assembly, photoablation, and/or molding techniques (see Thorsen, T., Maerkl, S. J., Quake, S. R., *Science* (2002) 298, 580; Jacobson, S. C., Culbertson, C. T., Daler, J. E., and Ramsey, J. M., *Analytical Chemistry* (1998) 70, 3476, which are incorporated herein at least for their teachings of forming microfluidic channels).

The disclosed microfluidic channels can have a variety of shapes, which depend on the particular composition of the channel and substrate, the particular lipids, the desired size and shape of the membrane, the particular analysis to be performed, preference, and the like. For example, one or more of the disclosed microfluidic channels can have a width of from about 10 to about 500 µm, from about 50 to about 250 µm, or from about 100 to about 200 µm. For example, one or more of the disclosed microfluidic channels can have a width of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 µm, where any of the stated values can form an upper or lower endpoint when appropriate.

In another example, one or more of the disclosed microfluidic channels can have a height of from about 10 to about 500 µm, from about 50 to about 250 µm, or from about 100 to about 200 µm. In more examples, one or more of the disclosed microfluidic channels can have a height of about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410; 420; 430, 440, 450, 460, 470, 480, 490, or 500 µm, where any of the stated values can form an upper or lower endpoint when appropriate.

In still another example, one or more of the disclosed microfluidic channels can have a length of from about 1 to about 50 mm, from about 10 to about 40 mm, or from about 20 to about 30 mm. In particular, one or more of the disclosed microfluidic channels can have a height of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mm, where any of the stated values can form an upper or lower endpoint when appropriate.

Methods of Using the Device

The disclosed devices can be used to form and analyze membranes. Any lipid that forms a lipid bilayer can be used. Examples of lipids are disclosed elsewhere herein. It is contemplated that a single type of lipid or mixtures of lipids can be used. Typically, though not necessarily, an aqueous solution is removed from the device for storage, leaving only the membrane precursor. When the device is to be used, immobilization of the membrane precursor is reversed and an aqueous solution is added to the microfluidic channels. The aqueous solution often contains buffers, preservatives, proteins or other biomolecules of interest, and the like.

The movement of liquid through the microfluidic channels can be controlled in any manner known to one of ordinary skill in the art. For example, liquid can be moved through the microfluidic channels with syringe pumps, by applying a vacuum, by applying an electric potential, by allowing a gas to flow over and/or through the microfluidic channels. Also, temperature gradients can move volumes of solutions through the microfluidic channels.

The disclosed device can also be integrated with a detection apparatus to monitor the formation, stability, and other characteristics of the bilayer, or various interactions between compounds as disclosed herein. Suitable detection apparatus are known in the art and include, for example, an optoelectronic detector, UV detector, refractive index detector, fluorescence detector, conductivity detector, electrochemical detector, FTIR detector, thermal conductivity detector, flame ionization detector, photoionization detector, mass spectroscopy detector, colorimetric detector, and other common analytical detectors known to one of ordinary skill in the art. The choice of the detection apparatus can be determined by one of ordinary skill in the art depending on the device, the lipid bilayer, any additional components or compounds, the property being measure, and the like.

It should be appreciated that measurements and observations of lipid bilayers formed from such frozen membrane precursors show that they have similar properties to conventionally formed bilayers and can be sufficiently robust to be withstand shipping and long-term storage.

Specific Examples

In one example, hexadecane is used to prepare a membrane precursor that can be applied to an orifice (i.e., a microfluidic channel in a substrate as disclosed herein). The temperature can then be lowered to less than about 17° C. (or the freezing point of the solvent of choice) before the solution thins into a membrane, thereby solidifying a membrane precursor. Such a precursor can remain in this state indefinitely, if so desired. Additionally, if desired, any remaining solution (or liquid) can be discarded, thereby leaving the frozen membrane precursor in a substantially dry state, which can simplify transport, if transport is desired.

In another example, a frozen membrane precursor can be converted into a membrane by heating the frozen membrane precursor to above about the freezing point of the solvent chosen for frozen membrane formation (e.g., in the previous example, hexadecane).

It will be apparent that a lipid bilayer membrane platform capable of long term storage and commercial shipping based on the solidification of a membrane precursor through freezing can be attained through the methods disclosed herein. The membranes formed using this system can be of high quality and can support the incorporation and measurement of ion channels at the single molecule level. The membrane precursors can be formed without operator feedback, meaning that this process can be automatable. Additionally, the equipment and processes for mass-production of the compositions disclosed herein can be simple and compact.

It should be appreciated that, by example, the total cost of the lipid, solvent, partition, and chamber materials in FIG. 1 was low enough to make the entire chamber and membrane apparatus optionally disposable. This formation technique combined with an inexpensive disposable apparatus makes possible a membrane-containing device which can be transported, indefinitely stored until desired use, and subsequently discarded. Because little, if any, expertise is necessary for membrane formation or integration with the measurement chamber, membrane and ion channel measurements can be accessed by a wider non-specialist audience, including those in the education or the pharmaceutical industry.

Possible applications of the methods and compositions disclosed herein include, but are not limited to, batch synthesis of biological or biomimetic membranes to be used in a low-cost, easy-to-use device for biophysical and biochemical experimentation/diagnostics of membranes and membrane proteins. This could be utilized by a wide variety of researchers and clinicians who do not have the equipment or expertise to perform these experiments with the existing technology.

Additional applications include low cost, mass production of membranes to house membrane proteins for high-throughput screening of targets for drug discovery.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, desired solvents, solvent mixtures, temperatures, pressures and other reaction ranges and conditions that can be used to optimize the methods described herein. Only reasonable and routine experimentation will be required to optimize such process conditions.

Example 1

General Materials and Methods

Membrane precursors were made by spreading a lipid solution containing 1% w/v lipid in 80:20 mixture of hexadecane:n-decane. 1,2-Diphytanoyl-sn-Glycero-3-Phosphatidylcholine (Avanti Polar Lipids) was used to make a membrane precursor solution without further purification. A TEFLON™ partition (Eastern Scientific) containing either 5 or 10 500 µm orifices was placed between two chambers. The TEFLON™ partition was pre-treated with 0.3% w/v DPhPC solution in n-decane. Each chamber was filled with 1 M KCl/1 mM EDTA buffered with 10 mM Tris.HCl at pH 8.5 and degassed. The membrane chip was machined from acrylic stock. The center partition was made from a thin (1 mm) low-density polyethylene (LDPE) film (Plastic Sheeting Supply Inc.). 500 µm holes were punched into the film using a hand-held micro punch (Ted-Pella Inc.). The LDPE partition, with hole, was then glued between two chamber halves.

Alpha-hemolysin (αHL) and gramicidin A (gA) (both from Sigma) were used for single channel measurements without further purification. To test protein activity, 1 µL of αHL (1.7 ng/µL) was added in one side of the chamber. gA was re-suspended in ethanol at 1 ng/mL. One µL of this solution was then added to the membrane precursor solution. In all cases, electrical measurements were made using Axopatch amplifier (Axon Instruments) with Ag/AgCl electrodes attached. Data was acquired and analyzed using pClamp and Clampfit software (Axon Instruments).

Example 2

Making a Biomimetic Membrane Precursor

A TEFLON™ chamber separated in two by a 15 µm-thick partition comprising an orifice 200 µm in diameter. The TEFLON™ chamber was then filled with an aqueous solution of 1 M KCl and 5 mM Hepes buffer adjusted to pH 7 in deionized water so that the hole is covered by the solution. A solution of 1 wt % DphPC in hexadecane was placed on the end of an applicator, such as a small pipette or glass rod and spread over the hole. The temperature was then lowered to below about 17° C., freezing the solution but not the surrounding water. At this point, the membrane precursor can be stored indefinitely, if so desired, or the water can be discarded, which can significantly increase the tolerance toward disruption and perturbation during shipping and/or handling.

Example 3

Making a Membrane from a Membrane Precursor

When desired, a frozen membrane precursor can be converted into a membrane by adding aqueous solution as described in Example 2, if the aqueous solution was discarded. The temperature can then be raised to about 17° C., if, for example, hexadecane was chosen as a solvent. After a certain time period, the membrane precursor can spontaneously thin to a lipid bilayer membrane. In certain aspects, such a membrane can be capable of supporting the incorporation and measurement of channel proteins (FIG. 1 b-d).

Example 4

Freezing a Biomimetic Membrane Precursor

Decane can be used for membrane formation using the Mueller-Rudin technique (Mueller et al., Nature, 194:979-980, 1962). Hexadecane has not been commonly used in this way, in part due to its higher viscosity. Interestingly, hexadecane has a freezing point at 18° C.—below room temperature but above the freezing temperature of water. A mixture of hexadecane and n-decane (80% v/v, respectively) containing 1 wt % 1,2-Diphytanoyl-sn-Glycero-3-Phosphatidylcholine ("MP" solution) was spread over the orifice as described previously (Albertorio et al., J. Am. Chem. Soc. 129:10567-10574, 2007). Prior to MP's spontaneous thinning to a lipid bilayer, it was cooled to about 4° C., freezing it. After thawing, the process of thinning to a bilayer membrane resumes (FIG. 1 b-d) and ultimately forms a functional bilayer. This process was tested on Teflon and polyethylene partitions incorporated into acrylic chambers.

Three variations of this concept were explored, changing the circumstances of MP application and storage in each instance. In the first, MP was spread over the aperture while it is submerged in buffer. When cooled to 4° C., MP froze completely while the buffer remained fluid. When returned to room temperature, MP thawed and the spontaneous thinning-out process resumed, forming a bilayer membrane (FIG. 1), which was monitored optically and electrically. Because MP was frozen in the presence of the aqueous solution and also stored in it, it was termed this variation "wet-wet."

The "wet-dry" variation of this process also involved application of MP to the orifice while it was submerged in buffer, but the buffer was discarded after MP was frozen. To create a lipid bilayer from the frozen and dry MP, cold (4° C.) buffer was added to the chamber. After warming, membrane formation proceeded as described above. Finally, in a "dry-dry" variation, about 5 µL of MP was dispensed directly onto the orifice without any buffer present and immediately cooled it below the freezing point of MP. Addition of cold buffer and thawing resulted in successful formation of bilayers as with the wet-dry membranes.

The temperature needed to freeze MP varied with its composition, ranging from 18° C. for 100% hexadecane to 14° C. for 80:20 hexadecane:decane. It is contemplated that other high freezing point solvent combinations can also work. The time required for this spontaneous thinning-out process ranged from 30 minutes up to 24 hours, increasing with increasing volumes of MP deposited and also dependent on the solvent composition, with pure hexadecane requiring the most time. Lipid bilayers formed with this technique usually remained stable for 12-24 hours.

TABLE 1

Success rate of bilayer membranes created
from frozen membrane precursors

| All membranes[a,c] | Stored over 30 days[a] |
|---|---|
| 72/264[b] | 6/13[b] |

[a]Membrane precursors stored 0-34 days.
[b]The number of membrane precursors thinned to make a lipid bilayer membrane/total membrane precursors stored.
[c]Shipped membrane precursors were included in the statistics.

Comparing membranes formed from the wet-wet, wet-dry, and dry-dry methods, no difference in method on the bilayer resistance and lifetime after thawing was observed. The probability of success also appeared to be roughly consistent across all techniques and did not depend on the time spent frozen (Table 1 and 2). Regardless of the method, all membranes that thinned to a bilayer with GΩ resistance could incorporate channel protein. The typical lifetime of the membranes listed in Table 1 was over 12 hours. When conventionally painting a membrane, the user can electrically or optically monitor the formation process and reapply the solution if needed, increasing the probability of obtaining a functional membrane. The process disclosed herein, however, does not allow this feedback to occur, and so the disclosed process success rates compare very favorably with traditional processes. It is contemplated that these rates can be further improved by optimizing the partition material as well as the volume of MP used.

TABLE 2

Success rate of shipped membranes created
from different deposition techniques

| Type of membrane precursor | Fraction of successful lipid bilayers created[d] |
|---|---|
| Wet-wet | 3/8 |
| Wet-dry | 9/17 |
| Dry-dry | 8/29 |

[d]Number of membrane precursors making a lipid bilayer typically lasting 12 hours/total number of membrane precursors shipped

Example 5

Handling Frozen Membrane Precursors in a Frozen State

The membrane precursors could be handled in the frozen state. To demonstrate the practical extent of this, the shipment of 54 frozen membrane precursors using a commercial carrier was conducted (see Table 2). These precursors, made using the wet-wet, wet-dry, and dry-dry methods, were prepared and frozen as described in the Examples above and packed in ice. Once received, the package was shipped back to a lab and delivered 2 days after the initial shipment. Membrane precursors from each method successfully resulted in lipid bilayers after thawing. Some of these shipped membrane precursors were stored in the frozen state for over a month after receipt and were subsequently seen to form membranes successfully.

Example 6

Method for Using a Membrane Formed from a Membrane Precursor

Figure 2:
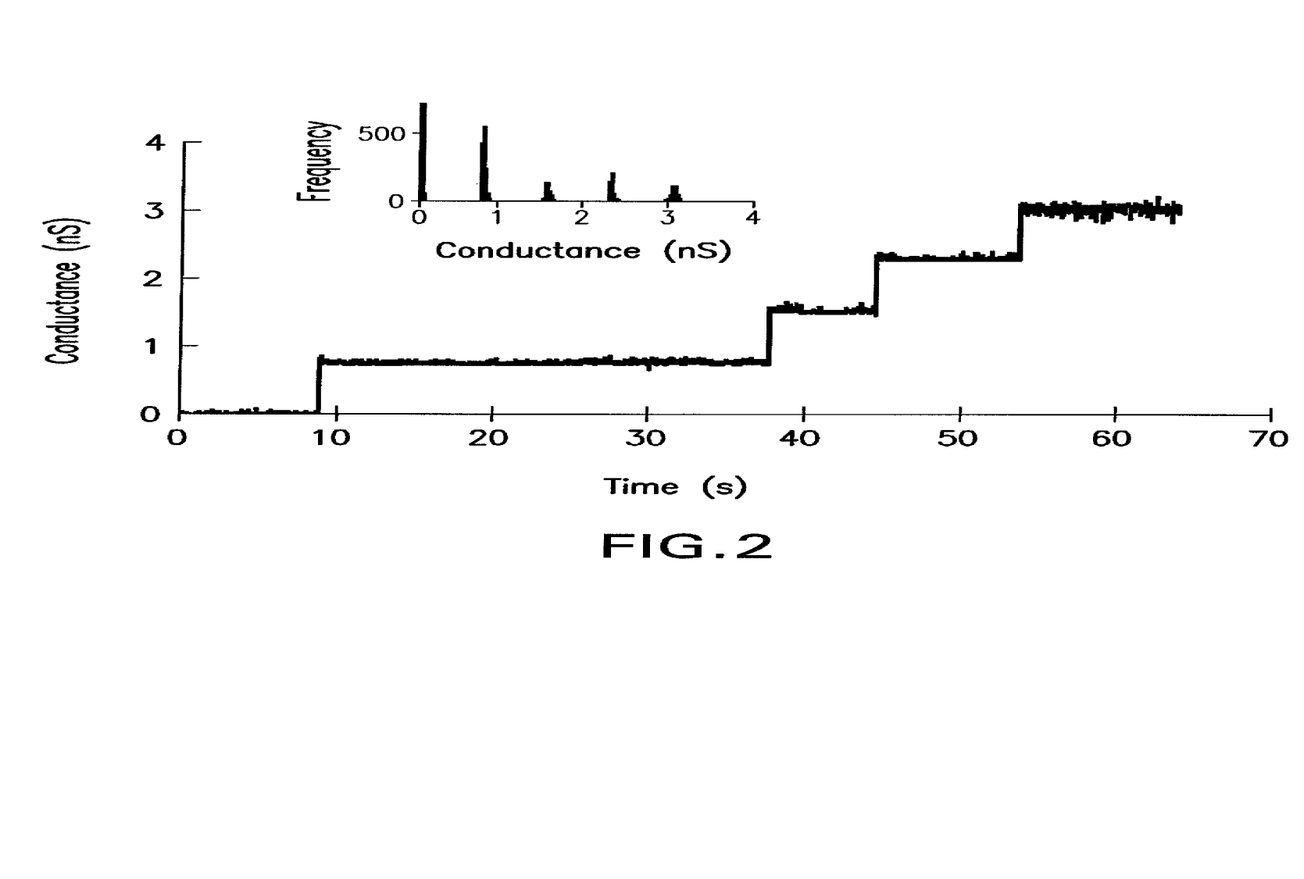
FIG. 2 shows α-Hemolysin channel activities on a lipid bilayer membrane created from a membrane precursor. The electrical potential across the membrane was applied at −40 mV. The data was filtered digitally at 100 Hz. Inset: a histogram of these data.
Figure 3:
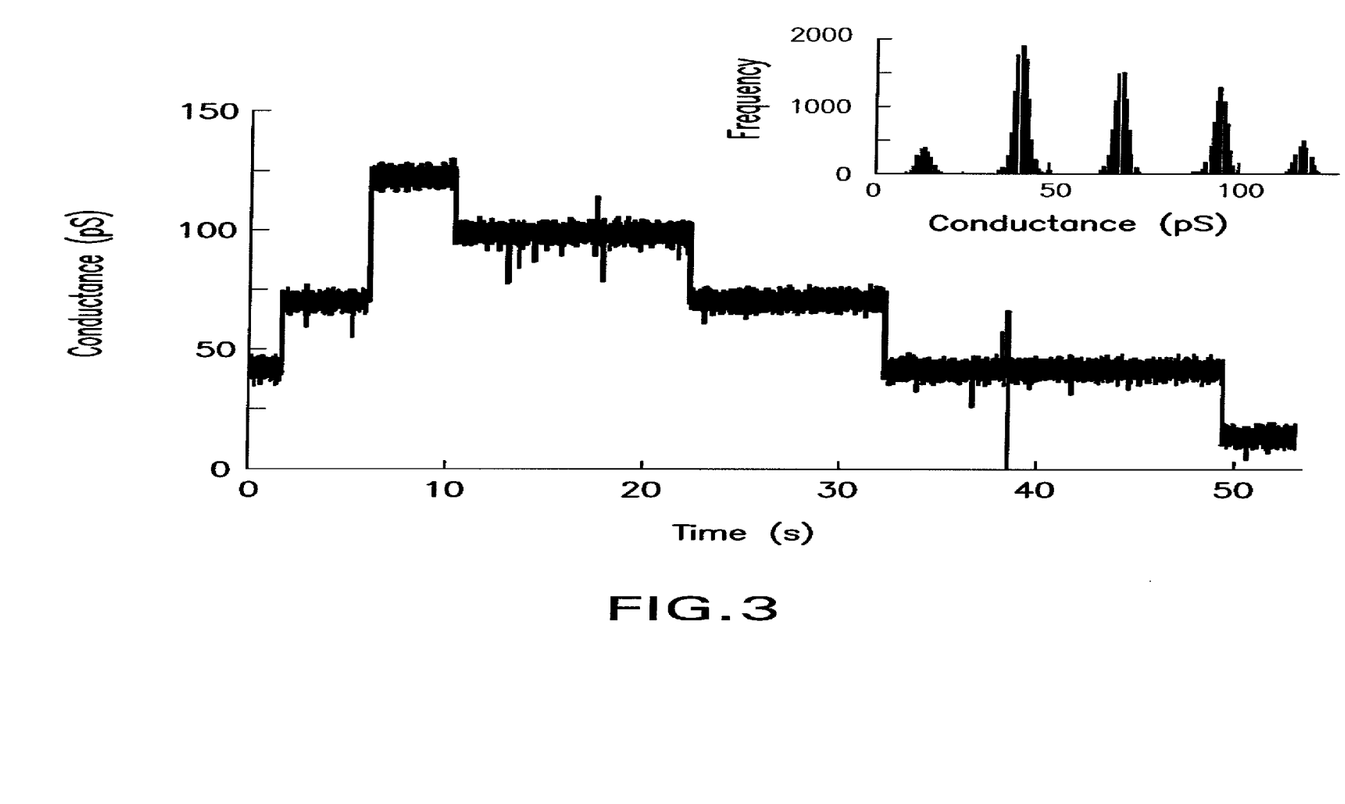
FIG. 3 shows measurement of the association/dissociation of gramicidin A dimers in a lipid bilayer created from a frozen membrane precursor solution containing gramicidin A. The applied electrical potential was −70 mV. The data were sampled at 5 KHz and further filtered digitally at 100 Hz. Inset: a histogram of these data.

To demonstrate the functionality of the lipid bilayers formed after freezing and thawing, the incorporation of ion channels gramicidin A (gA) and α-hemolysin into the lipid bilayers from the aqueous solution was measured (FIG. 2). To further reduce the system complexity and remove operator involvement from channel insertion, the possibility of introducing gA to MP before freezing and freezing the mixture was explored. Upon thawing, membranes formed from this mixture showed discrete channel currents due to the characteristic association/dissociation of gA dimers (FIG. 3).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device comprising:
   (a) a substrate;
   (b) one or more microfluidic channels; and
   (c) a membrane precursor deposited within the one or more microfluidic channel, wherein the membrane precursor comprises one or more lipids and one or more lipid immobilizers,
   wherein the one or more lipid immobilizers is in a solid or hydrogel form that immobilizes the one or more lipids, thereby preventing the formation of a functional bilayer membrane, and wherein the form of the one or more lipid immobilizers can be changed to a liquid form to reverse the immobilization of the one or more lipids, thereby allowing the formation of a functional bilayer membrane.

2. The device of claim 1, wherein the substrate comprises one or more of polyethylene, polypropylene, polystyrene, poly(meth)acrylate, polymethyl(meth)acrylate, polydivinylbenzene, fluorinated polydivinylbenzene, poly-N-vinylpyrrolidon, polyethylene terephthalate, cellulose acetate, polyamides, polyimide, polydimethylsiloxane, or polycarbonate.

3. The device of claim 1, wherein the one or more lipids comprises an ionic lipid.

4. The device of claim 1, wherein the one or more lipid immobilizers comprises one or more solvents with a melting point above about 4° C.

5. The device of claim 1, wherein the one or more lipid immobilizers comprises a hydrogel.

6. The device of claim 1, wherein the one or more lipid immobilizers comprises a hydrogel that turns into liquid when exposed to light.

7. The device of claim 1, wherein the one or more lipid immobilizers comprises a liquid that turns into a hydrogel when exposed to light.

8. The device of claim 1, wherein the membrane precursor further comprises a ligand, a protein, an antibody, a nucleic acid, or mixtures thereof.

9. The device of claim 1, further comprising a detection apparatus.

10. A method of forming a membrane precursor, comprising:
    (a) providing a device for preparing freestanding membranes, comprising a substrate, one or more microfluidic channels, and a membrane precursor deposited within the one or more microfluidic channels, wherein the membrane precursor comprises one or more lipids and one or more lipid immobilizers, wherein the one or more lipid immobilizers are in a liquid form; and (b) before the formation of a functional bilayer membrane, adjusting light, temperature, pH, pressure, or a mixture thereof to change the form of the one or more lipid immobilizers to a solid or hydrogel form that immobilizes the one or more lipids, thereby preventing the formation of a functional bilayer membrane.

11. The method of claim 10, further comprising:
(c) adjusting light, temperature, pH, pressure or a mixture thereof to reverse the immobilization of the one or more lipids in step (b), wherein the one or more lipids forms a functional bilayer membrane.

12. The method of claim 10, wherein the one or more lipids comprises an ionic lipid.

13. The method of claim 10, wherein the one or more lipids is a polymeric surfactant, silicon surfactant, fluorinated surfactant, oligomeric surfactant, dimeric surfactant, or natural lipid, or mixture thereof.

14. The method of claim 10, wherein the one or more lipid immobilizers comprises aminodextran, dextran, carboxymethyl dextran, DEAE-dextran, chondroitin sulfate, dermatan, dermatan sulfate, heparan, heparin, heparan sulfate, hyaluronic acid, chitosan, polyethyleneimine, polylysine, alginic acid, sodium alginate, pectin, gelatin, acid-hydrolytically-degraded gelatin, collagen, agarose, carrageenan, starch, polyvinyl alcohol, cellulose, methylcellulose, carboxymethylcellulose, hydroxypropylcellulose, polyacrylic acid, or mixtures thereof.

15. The method of claim 10, wherein the one or more lipid immobilizers comprises a PEG hydrogel with nitrobenzyl ether linker or PEG with coumarin chain ends.

16. The method of claim 10, wherein the one or more lipid immobilizers comprises a multi-vinyl PEG with vinyl chain ends or polyelectrolytes with cationic azobenzene surfactant.

17. The method of claim 10, wherein the one or more lipid immobilizers comprises a liquid that turns into a gel at temperatures above about 25° C.

18. The method of claim 10, wherein the one or more lipid immobilizers comprises a poly-N-isopropyl acrylamide or a copolymer thereof, or a block copolymer of polypropylene oxide and PEG.

19. The method of claim 10, wherein the one or more lipid immobilizers comprises a gel that turns into liquid at temperatures above about 4° C.

* * * * *